(12) United States Patent
Murata et al.

(10) Patent No.: US 11,825,856 B2
(45) Date of Patent: Nov. 28, 2023

(54) COMPOSITION FOR PREVENTING OR IMPROVING FUNCTIONAL GASTROINTESTINAL DISORDERS, AND, PHARMACEUTICAL COMPOSITION, FOOD/BEVERAGE COMPOSITION, AND METHOD OF PREVENTING OR IMPROVING FUNCTIONAL GASTROINTESTINAL DISORDERS USING THE COMPOSITION FOR PREVENTING OR IMPROVING FUNCTIONAL GASTROINTESTINAL DISORDERS

(71) Applicant: MORINAGA MILK INDUSTRY CO., LTD., Tokyo (JP)

(72) Inventors: Mai Murata, Zama (JP); Junichi Minami, Zama (JP); Hazuki Maehata, Zama (JP)

(73) Assignee: Morinaga Milk Industry Co., Ltd., Tokyo (JP)

(*) Notice: Subject to any disclaimer, the term of this patent is extended or adjusted under 35 U.S.C. 154(b) by 553 days.

(21) Appl. No.: 16/299,787

(22) Filed: Mar. 12, 2019

(65) Prior Publication Data
US 2019/0297909 A1  Oct. 3, 2019

(30) Foreign Application Priority Data
Mar. 28, 2018 (JP) .................. 2018-062467

(51) Int. Cl.
| | | |
|---|---|---|
| *A23C 9/123* | (2006.01) | |
| *A61K 35/745* | (2015.01) | |
| *A23L 33/135* | (2016.01) | |
| *A61P 1/00* | (2006.01) | |
| *A61P 25/00* | (2006.01) | |
| *A61K 9/00* | (2006.01) | |
| *A23K 10/18* | (2016.01) | |

(52) U.S. Cl.
CPC .......... *A23C 9/1234* (2013.01); *A23L 33/135* (2016.08); *A61K 9/0053* (2013.01); *A61K 35/745* (2013.01); *A61P 1/00* (2018.01); *A61P 25/00* (2018.01); *A23K 10/18* (2016.05); *A23V 2002/00* (2013.01); *A23V 2200/322* (2013.01); *A23V 2200/3204* (2013.01); *A23Y 2300/29* (2013.01)

(58) Field of Classification Search
CPC ........ A23V 2002/00; A23V 2200/3204; A23V 2200/322; A23V 2200/31; A23V 2200/32; A23C 9/1234; A23K 10/16; A23K 10/18; A23L 2/52; A23L 33/135; A23Y 2300/29; A61K 35/745; A61K 47/42; A61K 9/0053; A61K 9/0095; A61K 9/1658; A61K 9/19; A61P 1/00; A61P 25/00

See application file for complete search history.

(56) References Cited

U.S. PATENT DOCUMENTS

| | | | |
|---|---|---|---|
| 2002/0006432 A1* | 1/2002 | Collins | .............. A61P 35/00 424/439 |
| 2003/0092163 A1* | 5/2003 | Collins | .............. A61P 11/06 435/252.1 |
| 2011/0152517 A1 | 6/2011 | Tamaoki et al. | |
| 2012/0230956 A1 | 9/2012 | McLean et al. | |
| 2012/0308523 A1* | 12/2012 | Veiga | ................ A61P 1/00 424/93.3 |
| 2016/0206564 A1* | 7/2016 | Trachtman | ........ A61K 35/741 |
| 2017/0246225 A1* | 8/2017 | Shimizu | ............... A61P 3/04 |
| 2019/0083549 A1 | 3/2019 | Kobayashi et al. | |

FOREIGN PATENT DOCUMENTS

| | | |
|---|---|---|
| JP | 2014-101288 A | 6/2014 |
| JP | 2016-074682 A | 5/2016 |
| JP | 2018-184481 A | 11/2018 |
| WO | WO2010/035751 A1 | 4/2010 |
| WO | WO2017/209156 A1 | 12/2017 |

OTHER PUBLICATIONS

Urita, Y., et al., "Continuous consumption of fermented milk containing Bifidobacterium bifidum YIT 10347 improves gastrointestinal and psychological symptoms in patients with functional gastrointestinal disorders," Biosci. Microbiota Food Health 2015;34(2):37-44.

Office Action from Japanese Patent App. No. 2019-045011 (dated Nov. 1, 2022) with English language translation thereof.

Tabbers, M. M., et al., "Is Bifidobacterium breve effective in the treatment of childhood constipation? Results from a pilot study," Nutr. J. 2011;10(19):5 pp.

Quigley, E. M. M., "Bifidobacterium breve," The Microbiota in Gastrointestinal Pathophysiology, Chapter 15, 2017, Elsevier Inc., pp. 135-137.

(Continued)

*Primary Examiner* — Blaine Lankford
(74) *Attorney, Agent, or Firm* — Cermak Nakajima & McGowan LLP; Shelly Guest Cermak

(57) ABSTRACT

Provided is a composition for preventing or ameliorating a functional gastrointestinal disorder whose active ingredient is *Bifidobacterium breve* MCC1274 (FERM BP-11175). A composition for preventing or ameliorating a functional gastrointestinal disorder in the present technology can prevent or improve constipation or frequent bowel movements, regulate the number of bowel movements, improve stool quality, prevent or improve constipation, prevent or ameliorate bloating, or prevent or improve abdominal discomfort. Disclosed is a composition for preventing or ameliorating a functional gastrointestinal disorder accompanied by anxiety disorder. A composition for preventing or ameliorating a functional gastrointestinal disorder in the present technology can be used in a pharmaceutical composition or in a food or beverage composition.

7 Claims, 3 Drawing Sheets

(56) References Cited

OTHER PUBLICATIONS

Savignac, H. M., et al., "Bifidobacteria exert strain-specific effects on stress-related behavior and physiology in BALB/c mice," Neurogastroenterol. Motil. 2014;26:1615-1627.
Decision of Rejection from Japanese Patent Application No. 2019-045011 (dated Feb. 2, 2023) with English language translation.
Aloisio, I., et al., "Three-Month Feeding Integration With Bifidobacterium Strains Prevents Gastrointestinal Symptoms in Healthy Newborns"; Frontiers in Nutrition, May 2018, vol. 5, Article 39; p. 2158.

* cited by examiner

[FIG. 1]
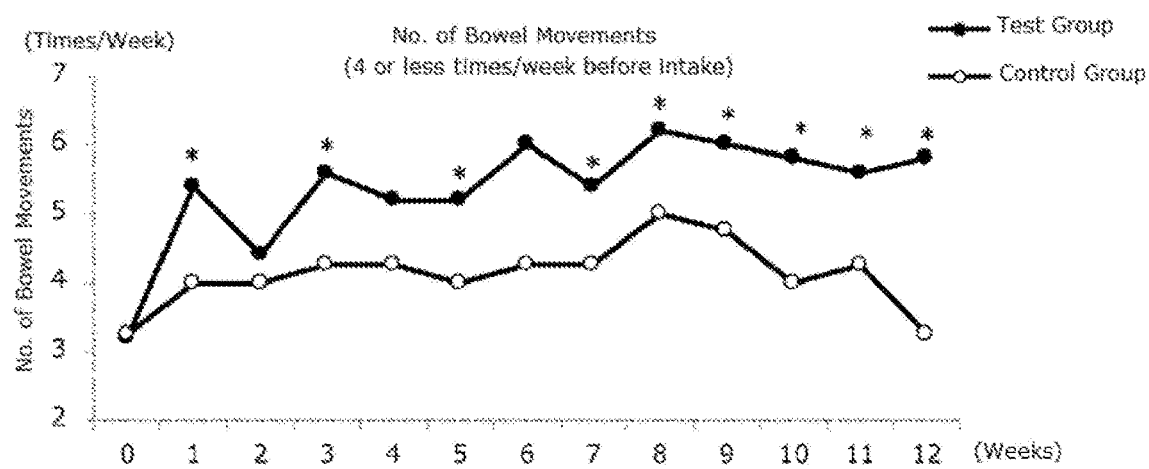
[FIG. 2]
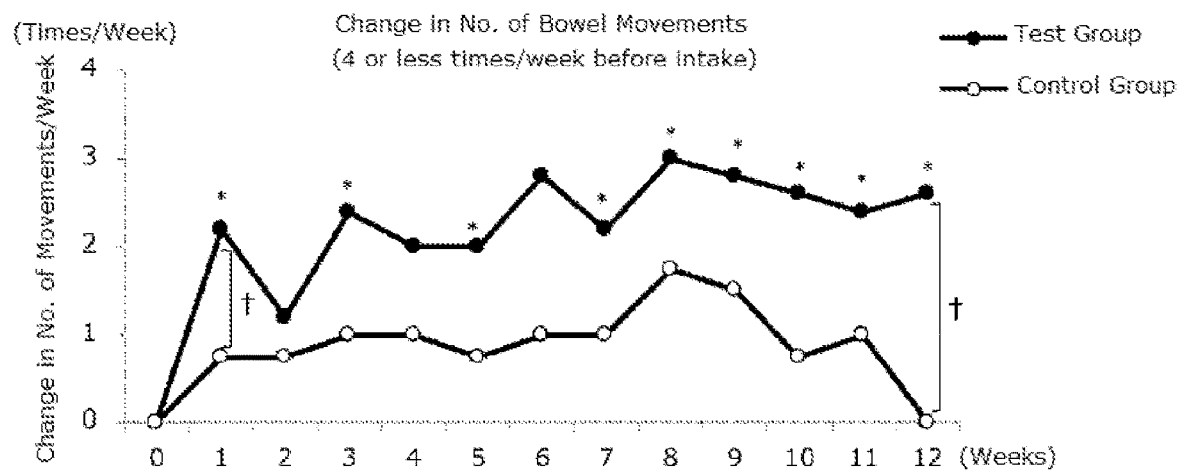

[FIG. 3]
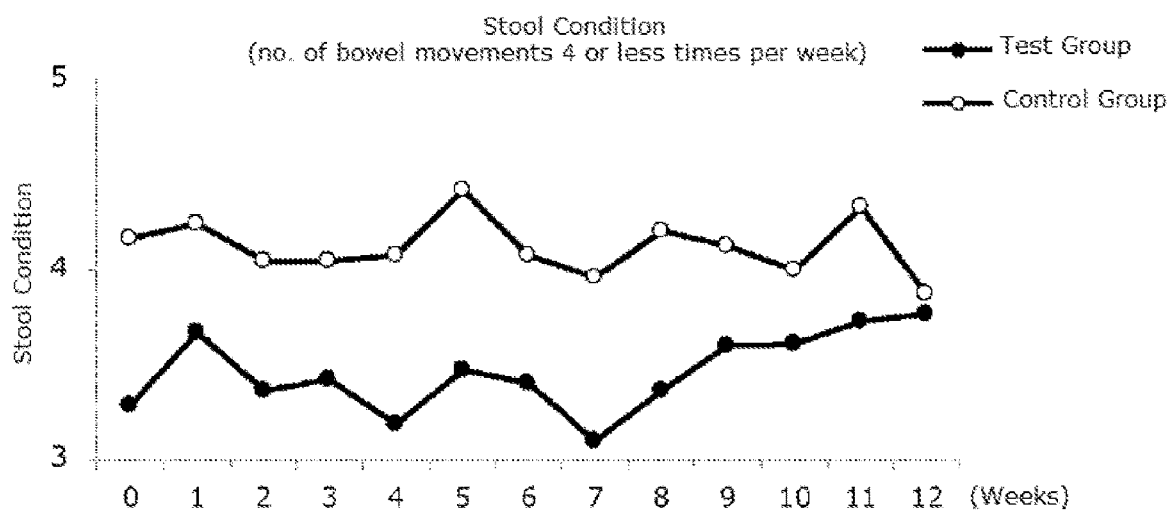
[FIG. 4]
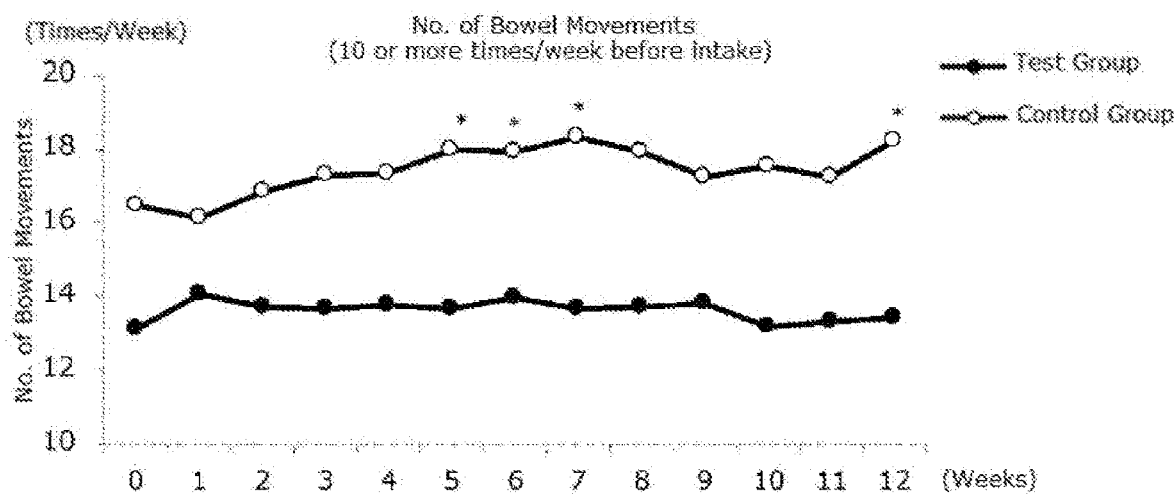

[FIG. 5]
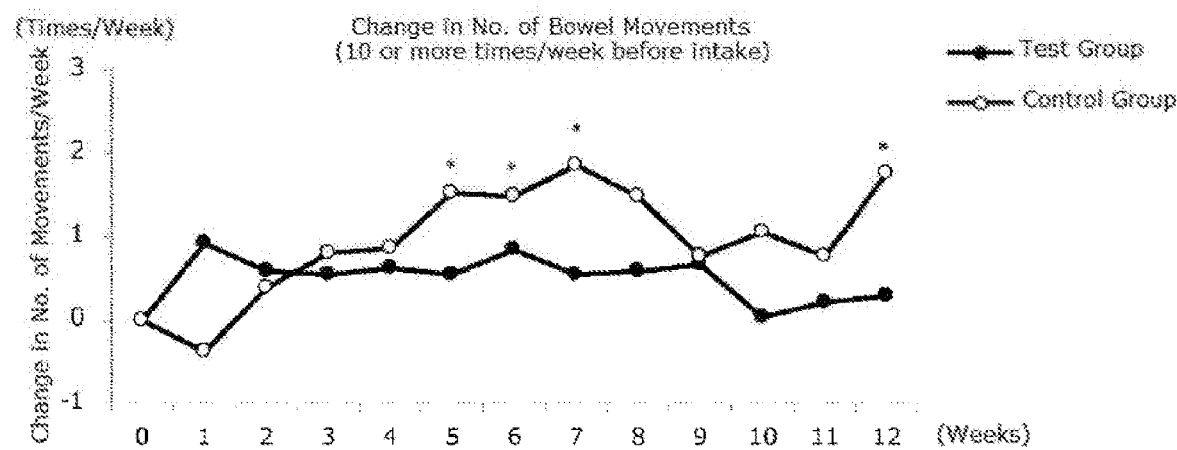
[FIG. 6]
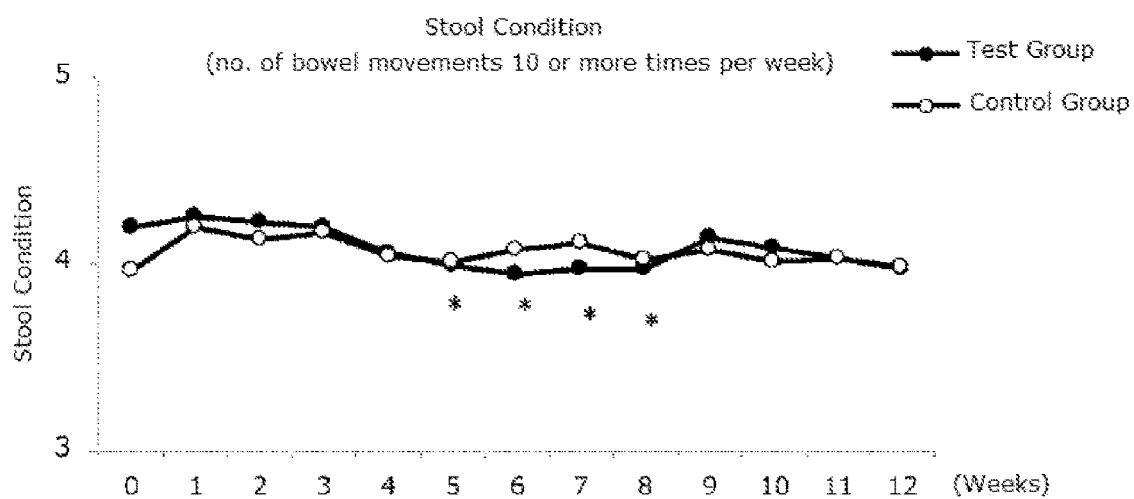

COMPOSITION FOR PREVENTING OR IMPROVING FUNCTIONAL GASTROINTESTINAL DISORDERS, AND, PHARMACEUTICAL COMPOSITION, FOOD/BEVERAGE COMPOSITION, AND METHOD OF PREVENTING OR IMPROVING FUNCTIONAL GASTROINTESTINAL DISORDERS USING THE COMPOSITION FOR PREVENTING OR IMPROVING FUNCTIONAL GASTROINTESTINAL DISORDERS

This application claims priority under 35 U.S.C. § 119 to Japanese Patent Application No. 2018-062467, filed Mar. 28, 2018, the entirety of which is incorporated by reference herein.

BACKGROUND

General Field

The present technology relates to a composition for preventing or ameliorating functional gastrointestinal disorders (FGIDs), a pharmaceutical composition and food or beverage composition using this composition for preventing or ameliorating functional gastrointestinal disorders, and a method for preventing or ameliorating functional gastrointestinal disorders.

Brief Description of the Related Art

While unpleasant subjective symptoms frequently occur from the chest to the abdomen in the case of functional gastrointestinal disorders (FGIDs), the abnormalities causing these symptoms have not been found and the number of patients experiencing these symptoms has been on the rise in recent years. The cause is believed to be related to several factors, including acid and food irritation in the digestive tract, visceral hypersensitivity, enterokinetic disorder, psychological and social stress, inflammation, and immunity, but it is not well understood.

Functional gastrointestinal disorders (FGIDs) known to be associated with anxiety and stress include irritable bowel syndrome (IBS) and functional dyspepsia (FD). IBS is a syndrome that starts with changes in bowel habits accompanied by abdominal discomfort, abdominal pain and bloating, and is characterized by chronically recurring diarrhea and/or constipation. Functional dyspepsia is associated with stomach and duodenal dysfunction whereas irritable bowel syndrome is primarily caused by dysfunction of the large intestine.

The prevalence of common FGIDs is high; 10-15% in the case of IBS and 10-44% in the case of FD. The occurrence of stress-induced FGIDs is a major social problem because it significantly reduces labor productivity and causes an economic burden.

Although there is much that we do not know about the pathophysiology of functional gastrointestinal disorders, functional dyspepsia is associated with such factors as genetic predisposition, *H. pylori* infection, psychosocial factors, infections, diet, and gastric acid. The mechanism of symptom manifestation includes adaptive relaxation disorder of the stomach fundus, gastric emptying disorder, and gastroduodenal hypersensitivity. In the case of irritable bowel syndrome, several studies have suggested the involvement of stress, enteric bacteria, mucosal inflammation, neurotransmitters, endocrine substances, psychological abnormalities, and genes (Oshima T., Miwa H., Japanese Journal of Occupational Medicine and Traumatology, 63: 270-275, 2015). An analysis of Japanese medical examinees indicates IBS causes a decrease on quality of life (QOL). It has also been shown that quality of life (QOL) improves when the pain associated with IBS is improved by treatment.

Attempts have been made to treat FD with antacids, prostaglandin derivatives, and gastrointestinal mucosal protective agents, but none of these therapeutic agents have been shown to be clearly effective. The use of synthetic chemical drugs such as psychotropics and anti-anxiety agents to relieve mental stress, sleep medications, internal neurotransmitter modulators (5-$HT_4$ stimulants, 5-$HT_3$ antagonists, dopamine $D_2$ blockers, anticholinergics, etc.) has also been suggested for IBS, but the effects are limited and none of them are suitable for daily or long-term use due to serious side effects and habit-forming properties. Although there have been attempts to address psychological stress, such as mental training, mind control, and cognitive behavioral therapy, their effectiveness is limited.

Symptoms do not always appear but, when these stresses are applied, dysfunction appears. Also, the strength and frequency of symptoms changes depending on individual responses to stress. In addition, symptoms in different locations along the gastrointestinal tract combine or symptoms change over time. Other problems occur, such as lower quality of life (QOL), lower productivity at work and in daily life, and increased medical expenses.

Thus, functional digestive tract disorders manifesting multiple, complicated symptoms are difficult to treat. Instead, so-called symptomatic treatments are performed in which drugs are administered based on the symptoms manifesting at the time while making lifestyle improvements.

In recent years, methods for preventing and treating functional gastrointestinal tract disorders have been proposed. For example, in JP 2018-184481 A, a preventive and/or therapeutic agent for functional gastrointestinal disorders containing rifaximin as an active ingredient has been disclosed.

Also, a technique has been disclosed in WO 2010/035751 A1 which can prevent and/or improve functional digestive tract disorders in both *H. pylori* positive and negative persons using *Lactobacillus* lactic acid bacteria, preferably *Lactobacillus gasseri*. JP 2014-101288 A discloses a suppressive effect on a stress-induced bowel disorders by using a bactericidal product of the *Lactobacillus gasseri* CP2305 strain as an active ingredient. JP 2016-074682 A discloses a composition for treating and/or preventing functional gastrointestinal (GI) disorders which contains the *Bifidobacterium longum* NCC3001 strain. Y Urita et al. (Biosci Microbiota Food Health. 2015; 34(2): 37)-44 discloses an effect of ameliorating gastrointestinal symptoms (abdominal pain, diarrhea, constipation, dyspepsia) and psychological stress in FGID patients from yogurt containing *Bifidobacterium bifidum* strain YIT 10347.

SUMMARY

Technical Problem

As mentioned above, many methods for preventing and treating functional gastrointestinal tract disorders have been proposed. However, methods using synthetic compounds such as the one in JP 2018-184481 A raise concerns about side effects. Also, methods for preventing or treating functional gastrointestinal disorders by ingesting probiotic microorganisms or fermentation products have been reported, such as the one described in WO 2010/035751 A1, but probiotics are known to exhibit different physiological effects in different strains and consistent results have not been obtained in these reports. Furthermore, improvements in anxiety, mental symptoms, and gastrointestinal symptoms from probiotics have been limited.

Therefore, it is a primary object of the present technology to provide a novel composition for preventing or ameliorating functional gastrointestinal disorders.

Solution to Problem

Specifically, the present technology provides a composition for preventing or ameliorating a functional gastrointestinal disorder whose active ingredient is *Bifidobacterium breve* MCC1274 (FERM BP-11175). A composition according to the present technology prevents or improves constipation or frequent bowel movements, regulates the number of bowel movements, improves stool quality, prevents or improves constipation, prevents or ameliorates bloating, or prevents or improves abdominal discomfort. In addition, a composition of the present technology relieves stress and/or anxiety symptoms. Specifically, it has the effect of preventing or ameliorating anger, confusion, tension or fatigue, or improving vitality.

A composition of the present technology can be used in a pharmaceutical composition or in a food or beverage composition. When a composition of the present technology is used in a pharmaceutical composition or in a food or beverage composition, the composition comprises from $10^6$ to $10^{12}$ cfu of *Bifidobacterium breve* MCC1274 (FERM BP-11175) per packaging unit or per serving. The food composition can be a yogurt or infant formula.

The present technology is also the use of *Bifidobacterium breve* MCC1274 (FERM BP-11175) in an agent for preventing or ameliorating a functional gastrointestinal disorder, a pharmaceutical for preventing or ameliorating a functional gastrointestinal disorder, or a food or beverage product for preventing or ameliorating a functional gastrointestinal disorder. Proposed are a method for preventing or ameliorating a functional gastrointestinal disorder, the method comprising administering *Bifidobacterium breve* MCC1274 (FERM BP-11175) to the subject; a method for preventing or ameliorating a functional gastrointestinal disorder, the method comprising administering *Bifidobacterium breve* MCC1274 (FERM BP-11175) to a subject with normal brain function; a method for preventing or ameliorating a functional gastrointestinal disorder, the method comprising administering *Bifidobacterium breve* MCC1274 (FERM BP-11175) to a person who is 35 years of age or older; and a method for preventing or ameliorating a functional gastrointestinal disorder, the method comprising administering *Bifidobacterium breve* MCC1274 (FERM BP-11175) to a subject during the autumn and winter seasons.

Advantageous Effects

The present technology is able to provide a novel composition for preventing or ameliorating functional gastrointestinal disorders. The disclosed subject matter is not limited to the effect described here but also includes any other effect mentioned herein.

BRIEF DESCRIPTION OF THE DRAWINGS

FIG. 1 is a graph showing the effect of Example 1 on the number of bowel movements in subjects who had four or fewer bowel movements per week prior to intake.

FIG. 2 is a graph showing the effect of Example 1 on the change in the number of bowel movements in subjects who had four or fewer bowel movements per week prior to intake.

FIG. 3 is a graph showing the effect of Example 1 on stool quality in subjects who had four or fewer bowel movements per week prior to intake.

FIG. 4 is a graph showing the effect of Example 1 on the number of bowel movements in subjects who had ten or more bowel movements per week prior to intake.

FIG. 5 is a graph showing the effect of Example 1 on the change in the number of bowel movements in subjects who had ten or more bowel movements per week prior to intake.

FIG. 6 is a graph showing the effect of Example 1 on stool quality in subjects who had ten or more bowel movements per week prior to intake.

DESCRIPTION OF THE EXEMPLARY EMBODIMENTS

The following is a description of exemplary embodiments of the present technology. The embodiments described below are typical examples of embodiments of the present technology and should not be interpreted as narrowing the scope of the present technology in any way.

1. Composition for Preventing or Ameliorating Functional Gastrointestinal Disorder A composition for preventing or ameliorating a functional gastrointestinal disorder in the present technology is characterized by the used of *Bifidobacterium breve* MCC1274 (FERM BP-11175) as an active ingredient.

*Bifidobacterium breve* MCC1274 was deposited on Aug. 25, 2009 under Accession Number IPOD FERM BP-11175 at the National Institute of Technology and Evaluation-International Patent Organism Depositary (NITE-IPOD), Central 6, 1-1-1, Higashi, Tsukuba, Ibaraki, Japan 305-8566 (Current location: Room 120, 2-5-8, Kazusakamatari, Kisarazu, Chiba 292-0818, Japan), and can be obtained from this organization.

Note that the aforementioned bacteria name is not limited to the strain that was deposited and registered at the aforementioned organization under this name, but also includes substantially equivalent strains (referred to as "derived strains" or "induced strains"). Specifically, "MCC1274 (FERM BP-11175)" is not limited to the strain deposited at the depositary under the accession number for MCC1274 (FERM BP-11175), but includes all substantially equivalent strains. Here, "a strain substantially equivalent to the deposited strain" means a strain which belongs to the same species as the deposited strain and from which the sleep-promoting effect that is an effect can be obtained. A strain substantially equivalent to the deposited strain can be, for example, a derivative strain having the deposited strain as the parent strain. Derivative strains include strains bred from deposited strains and strains produced naturally from deposited strains.

The substantially equivalent strains and derivative strains include the following.

(1) Strains deemed as identical to *Bifidobacterium breve* MCC1274 using the (randomly amplified polymorphic DNA (RAPD) method and the pulsed-field gel electrophoresis (PFGE) method (see Probiotics in food/Health and nutritional properties and guidelines for evaluation 85, Page 43).

(2) Strains having only genes derived from *Bifidobacterium breve* MCC1274, no foreign genes, and a DNA identity of 95% or more with *Bifidobacterium breve* MCC1274.

(3) Strains bred from *Bifidobacterium breve* MCC1274 (including strains bred by genetic engineering modification, mutation, and spontaneous mutation) and having the traits of MCC1274.

*Bifidobacterium breve* (*Bifidobacterium breve*) is only one of the bacterial species belonging to the genus *Bifidobacterium*. *Bifidobacterium breve* lives primarily in the large intestine of infants, and is known among the bacteria belonging to the genus *Bifidobacterium* as an infant-type *Bifidobacterium* along others such as *Bifidobacterium longum* subsp. *infantis*.

Because the composition for preventing or ameliorating functional gastrointestinal tract disorders in the present technology is *Bifidobacterium breve*, whose active ingredient primarily resides in the large intestine of infants and children, it is safe and effective and side effects are not a concern even during long-term, continuous administration.

In the present specification, "alleviation" means reversal of a symptom or disease, prevention or delay in deterioration of a symptom or disease, reversal, prevention or delay in the progression of a symptom or disease, or treatment of a symptoms or disease. In the present specification, "alleviation" may also mean prevention. Here, "prevention" means preventing or delaying the onset of a symptom or disease in a subject, or reducing the risk of developing a symptom or disease in a subject.

Compositions for preventing or ameliorating functional gastrointestinal tract disorders in the present technology have an effect on functional gastrointestinal disorders selected from the group consisting of non-erosive reflux disease (NERD), functional dyspepsia (FD), Irritable bowel syndrome (IBS), functional constipation, functional diarrhea, functional abdominal pain, functional abdominal distension, epigastric pain syndrome (EPS), postprandial distress syndrome (PDS), or combinations thereof. In particular, the compositions have an effect of preventing or ameliorating specific symptoms, including improving constipation or ameliorating frequent bowel movements, regulating the number of bowel movements, improving stool quality, preventing or ameliorating constipation, preventing or ameliorating bloating, or preventing or ameliorating abdominal discomfort.

<Definitions of Diseases>

In the present technology, functional gastrointestinal tract disorders can be evaluated by examining the number of bowel movements, stool quality, upper abdominal symptoms, abdominal pain, and abdominal discomfort at a given point in time or over time. For example, the Rome IV diagnostic criteria listed below can be used as international diagnostic criteria for functional gastrointestinal disorders such as IBS, FD, EPS, and PDS.

Diagnostic Criteria for Irritable Bowel Syndrome (IBS)

Over the most recent three months, abdominal pain has recurred four days or more per month, and two or more of the following have occurred.
1. Symptoms are related to bowel movements
2. Changes have occurred in the frequency of bowel movements
3. Changes have occurred in stool quality.

Some of the symptoms have occurred for more than six months, and these criteria have been met over the most recent three months.

Classification of Irritable Bowel Syndrome (IBS)
1. Constipation-Type IBS (IBS-C):
   25% or more of bowel movements are hard stools or pellets, and fewer than 25% of bowel movements are soft (muddy) or watery
2. Diarrhea-Type IBS (IBS-D):
   25% or more of bowel movements are soft (muddy) or watery, and fewer than 25% of bowel movements are hard stools or pellets
3. Mixed IBS (IBS-M):
   25% or more of bowel movements are hard stools or pellets, and 25% or more of bowel movements are soft (muddy) or watery
4. Unclassifiable IBS:
   The criteria for abnormal stool quality do not meet the criteria for IBS—C, IBS-D, or IBS-M.

Classification of Functional Constipation

Two or more of the following six items are met.

Three or more months of persistent or recurring functional bowel disease that does not meet the diagnostic criteria for IBS described above. Constipation without a stomachache is known as functional constipation.
1. More than one-quarter of bowel movements require strong effort.
2. More than one-quarter of bowel movements are hard stools or pellets.
3. More than one-quarter of bowel movements feel incomplete.
4. More than one-quarter of bowel movements feel obstructed and difficult to evacuate.
5. More than one-quarter of bowel movements require manual assistance.
6. The number of voluntary bowel movements is fewer than 3 times a week.

Classification of Functional Diarrhea

Functional diarrhea is a persistent or recurring syndrome that lasts at least three months in which more than one-quarter of bowel movements being soft (muddy) or watery stools. It is a functional bowel disease characterized by no abdominal pain or abdominal discomfort and does not meet the diagnostic criteria for IBS described above.

Diagnostic Criteria for Functional Dyspepsia (FD)

Any of the following symptoms begin at least six months before diagnosis and are present over the past three months.
1. Distressing epigastric pain
2. Distressing epigastric burning
3. Distressing postprandial fullness
4. Distressing sense of early satiety Also, there is no organic disease that can explain the symptoms.

Diagnostic Criteria for Postprandial Distress Syndrome (PDS)

One or two of Items 1 and 2 below are met at least three days a week.
1. Distressing postprandial fullness
2. Distressing sense of early satiety Diagnostic Criteria for Epigastric Pain Syndrome (EPS)

One or two of Items 1 and 2 below are met at least one day a week.
1. Distressing epigastric pain
2. Distressing epigastric burning Functional gastrointestinal disorders are also related to psychological and social factors such as the stress of everyday life, so the compositions for preventing or ameliorating functional gastrointestinal disorders in the present technology can also have an effect of alleviating stress and/or anxiety related to the effects described above. Functional gastrointestinal disorders are often triggered by psychological disorders such as stress, and are often accompanied by anxiety disorders and depression. The administration of a composition for preventing or ameliorating functional gastrointestinal disorders according to the present technology can alleviate stress and/or anxiety disorders. Specifically, such a composition can have an effect of preventing or ameliorating anger, confusion, tension or fatigue, or improving vitality.

In the present technology, stress can be evaluated using POMS (Profile of Mood States) or POMS2 (Profile of Mood States, 2nd Edition). POMS and POMS 2 are registered trademarks of Multi-Health Systems Inc. Both versions of this psychological test use different examination methods depending on the target population, such as adults or adolescents, and have a different number of examination questions in the full version and short version. The examination method and number of questions selected depends on the condition of the subject.

The following factors are measured in POMS: Anger-Hostility (AH), Confusion (C), Depression-Dejection (DD), Fatigue (F), Tension-Anxiety (TA), Vigor (V), and Total Mood Disturbance (TMD).

The following factors are measured in POMS 2: Anger-Hostility (AH), Confusion-Bewilderment (CB), Depression-Dejection (DD), Fatigue-Inertia (FI), Tension-Anxiety (TA), Vigor-Activity (VA), Friendliness (F), and Total Mood Disturbance (TMD).

There are no particular restrictions on the subject receiving a composition for preventing or ameliorating functional gastrointestinal disorders according to the present technology; it can be an animal including humans. There are no particular age or sex restrictions but, in the case of humans, it is especially effective on middle-aged persons 35 years of age or older, preferably 40 years of age or older, and more preferably 45 years of age or older. School children, such as primary school students, junior high school students, and high school students, also have functional gastrointestinal disorders, and these are a major cause of stomachache in children. A composition according to the present technology can be administered to school children. A composition according to the present technology can also be used to alleviate abdominal symptoms such as diarrhea, constipation, and abdominal pain in women during pregnancy, during the perinatal and lactation periods, and before and after menstruation. A composition according to the present technology is preferably administered to the following subjects.

(1) Persons who are conscientious, serious and responsible, work hard and have a strong sense of justice, have a hard time saying no, hate interpersonal conflict, always consider other persons' feelings, and are prone to depression
(2) Persons who are vulnerable to environmental changes
(3) Persons who are sensitive to stress
(4) Persons who have difficulty with interpersonal relationships and friendships A composition for preventing or ameliorating functional gastrointestinal disorders according to the present technology can be used anytime throughout the year, but is especially effective during the change of seasons and during the autumn and winter months, which can be particularly stressful.

The *Bifidobacterium breve* MCC1274 (FERM BP-11175) serving as the active ingredient in a composition for preventing or ameliorating a functional gastrointestinal disorder in the present technology may be a culture including *Bifidobacterium breve* MCC1274 (FERM BP-11175).

There are no particular restrictions on the medium for culturing the *Bifidobacterium breve* used in the present technology. It can be any medium commonly used for culturing bacteria belonging to the genus *Bifidobacterium*.

The carbon source can be saccharides such as glucose, galactose, lactose, arabinose, mannose and sucrose, starches, starch hydrolysates, and waste molasses depending on assimilability. Ammonia, ammonium salts such as ammonium sulfate, ammonium chloride and ammonium nitrate, and nitrates can also be used as the carbon source. Inorganic salts that can be used include sodium chloride, potassium chloride, potassium phosphate, magnesium sulfate, calcium chloride, calcium nitrate, manganese chloride, and ferrous sulfate. In addition, organic components such as peptones, soybean powders, defatted soybean meal, meat extracts, and yeast extracts can be used.

There are no particular restrictions on the culturing conditions as long as the effect of the present technology is not impaired. The culture temperature is usually from 25 to 50° C., and preferably from 35 to 42° C. The culture is preferably cultured under anaerobic conditions. For example, it can be cultivated while supplying an anaerobic gas such as a carbon dioxide gas. However, the culture may also be cultivated under microaerophilic conditions, such as in a stationary liquid culture.

The *Bifidobacterium breve* used in the present technology may be used in the form of the resulting culture with or without dilution or concentration, or the bacteria may be collected from the resulting culture and used.

The bacteria may be used in the resulting culture with or without dilution or concentration, or the bacteria may be collected from the resulting culture and used. Other operations such as heating and freeze-drying can be performed after culturing as long as the effects are not impaired. The bacteria may be alive or dead. Live bacteria are preferably subjected to the bacterial solution freezing method, the spray drying method, the freeze-drying method, or the oil drop method. Dead bacteria may be sterilized by heat or freeze-drying. Other methods that can be used to prepare dead bacteria include the spray drying method (spray dry method), retort sterilization method, freeze-drying method, UHT sterilization method, pressure sterilization method, high pressure steam sterilization method, dry heat sterilization method, distributed steam disinfection method, electromagnetic wave sterilization method, electron beam sterilization method, high frequency sterilization method, radiation sterilization method, UV sterilization method, ethylene oxide gas sterilization method, hydrogen peroxide gas plasma sterilization method, and chemical sterilization method (alcohol sterilization method, formalin fixation method, electrolytic water treatment method). The bacteria may also be disrupted. The bacteria can be disrupted while live or dead, and heated or freeze-dried after disruption. The disruption can be performed using physical crushing, enzyme dissolution, chemical processing, or autolysis using methods and equipment common in the art. Physical disruption may be performed in the form of a suspension or powder. The physical disruption can be performed by agitation using an ultrasonic homogenizer, homogenizer, ball mill, bead mill, dyno mill or planetary mill, under pressure using a jet mill, French press or cell disruptor, or by cellular damage using filtration. In an enzyme dissolution treatment, an enzyme such as lysozyme can be used to disrupt the cell structure of the lactic acid bacterial cells. In chemical treatment, a surfactant such as a soybean phospholipid or glycerin fatty acid ester can be used to disrupt the cell structure of lactic acid bacterial cells. In autolysis, lactic acid bacterial cells can be dissolved using some of the enzymes of the lactic acid bacteria themselves. Physical disruption is preferred because other chemicals and compounds do not have to be added.

In the present specification, "culture" includes the culture supernatant.

A composition for preventing or ameliorating a functional gastrointestinal disorder according to the present technology can be the active ingredient alone or a composition containing any ingredient along with the active ingredient. There are no particular restrictions on the other ingredients can be any additive commonly used in pharmaceutical products (such as the pharmaceutical carriers described later).

2. Specific Forms of Compositions for Preventing or Ameliorating Functional Gastrointestinal Disorders in the Present Technology A composition for preventing or ameliorating a functional gastrointestinal disorder according to the present technology can assume the form of a food or beverage product, a pharmaceutical product, a quasi-drug, or a feed.

The purpose of the present embodiment can be therapeutic or non-therapeutic. A "non-therapeutic purpose" is a concept that does not include the practice of medicine, that is, the treatment of the human body with therapy. Examples include the promotion of health and enhancement of beauty. Here, "alleviation" means reversal of a symptom or disease, prevention or delay in deterioration of a symptom or disease, or reversal, prevention or delay in the progression of a symptom or disease. Here, "prevention" means preventing or delaying the onset of a symptom or disease in a subject, or reducing the risk of developing a symptom or disease in a subject.

<Food and Beverage Products>

A composition for preventing or ameliorating a functional gastrointestinal disorder according to the present technology can be added to an existing food or beverage product or mixed with the ingredients of a food or beverage product to prepare a novel food or beverage product.

Food or beverage products using a composition for preventing or ameliorating a functional gastrointestinal disorder according to the present technology can be in liquid, paste, solid, or powdered form. In addition to tablet cakes and liquid foods, examples include commercially available products such as flour products, instant foods, agricultural products, fish products, meat products, milk and dairy products, fats and oils, basic seasonings, mixed seasonings/foodstuffs, frozen foods, confectioneries, and beverages.

Examples of flour products include breads, macaroni, spaghetti, noodles, cake mixes, fried flour, and bread crumbs. Instant foods include instant noodles, cup noodles, retort packaged foods, canned foods, microwave foods, instant soups, instant miso soups, canned soup, and freeze-dried foods. Agricultural products such as canned agricultural products, canned fruits, jams and marmalades, pickles, boiled beans, dry agricultural products, and cereals (processed grain products). Fish products include canned fish, fish filets and sausages, fish pastes, seafood delicacies, and tsukudani. Meat products include canned meat and pastes, and meat filets and sausages. Milk and dairy products include fermented milk products such as yogurt, processed milk, milk beverages, lactic acid bacteria beverages, cheeses, ice creams, powdered milks, creams, powdered milk formulas for children, infant food supplements, and mother's milk for pregnant women and nursing women. Oils and fats include butters, margarines, and vegetable oils. Examples of basic seasonings include soy sauce, miso, sauces, tomato-based seasonings, mirin, and vinegar. Examples of mixed seasonings/foodstuffs include cooking mix, curry ingredients, sauces, dressings, noodles, and spices. Examples of freeze-dried foods include raw frozen foods, semi-cooked frozen foods, and cooked frozen foods.

Confectioneries include caramels, candies, chewing gum, chocolates, cookies, biscuits, cakes, pies, snacks, crackers, Japanese sweets, rice cakes, bean candies, and dessert sweets. Examples of beverages include soft drinks, natural juices, juices, soft drinks containing juices, broths, fruit drinks with berries, vegetable drinks, soymilk, soy milk beverages, coffee drinks, tea drinks, powdered beverages, concentrated beverages, sports drinks, health drinks, and alcoholic beverages. Other commercially available food products include baby foods, sprinkled-on seasonings, and chazuke drinks. A food or beverage composition can be prepared by adding the bacteria to the raw materials of a food or beverage product, or prepared in the same manner as an ordinary food or beverage product except for the addition of the bacteria. The bacteria can be added at any stage of the food or beverage preparation process. A food or beverage product may also be prepared via a fermentation step using the bacteria. Examples of such food or beverage products include lactic acid bacteria drinks and fermented milk products.

The raw materials used in these food and beverage compositions can be any raw material commonly used in food and beverage products. The resulting food or beverage composition can be ingested orally.

Also, the bacteria can be added to pumped breast milk for oral ingestion by newborns and infants or for ingestion by nasogastric feeding tube.

A food or beverage composition can be a component known or likely to be found to have a probiotic effect or a component that assists with a probiotic effect, as long as the effects are not impaired. Examples of food and beverage compositions include proteins such as whey protein, casein protein, soy protein and pea protein (pea protein), as well as mixtures and degradation products thereof; amino acids such as leucine, valine, isoleucine or glutamine; vitamins such as vitamin B6 or vitamin C; creatine; citric acid; fish oils; and oligosaccharides such as isomaltooligosaccharides, galactooligosaccharides, xylooligosaccharides, soybean oligosaccharides, fructooligosaccharides, lactulose, and human milk oligosaccharides (HMO) combined with the bacteria. Human milk oligosaccharides that can be used include neutral human milk oligosaccharides such as 2'-fucosyl lactose, 3-fucosyl lactose, 2',3-difucosyllactose, lacto-N-triose II, lacto-N-tetraose, lacto-N-neotetraose, lacto-N-fucopentaose I, lacto-N-neofcopentaose, lacto-N-fucopentaose II, lacto-N-fucopentaose III, lacto-N-fucopentaose V, lacto-N-neofcopentaose V, lacto-N-difucohexaose I, lacto-N-difucohexaose II, 6'-galactosyl lactose, 3'-galactosyl lactose, lacto-N-hexaose, and lacto-N-neohexaose, as well as acidic human milk oligosaccharides such as 3'-sialyllactose, 6'-sialyl lactose, 3-fucosyl-3'-sialyl lactose, and disialyl-lacto-N-tetraose.

A food or beverage product according to the present technology can also be infant formula. Different types of infant formula include infant formula for infants from 0 to 12 months, follow-up milk for infants from 6 to 9 months and small children (up to 3 years old), low birth weight infant formula for newborns weighing less than 2,500 g at birth (low birth weight infants), and therapeutic milks used to treat children with conditions such as milk allergies and lactose intolerance. A composition according to the present technology can also be applied to functional health foods and patient foods. Because functional health foods are administered in the form of a tablet, capsule, or ordinary food product depending on market trends at home and abroad and in conformity with existing health food regulations, they are generally classified as specialized health foods (requiring individual approval) and nutritive function food products (subject to standard criteria).

Examples of food and beverage products according to the present technology include mother's milk (powdered milk formula) and nutritional supplements for women during pregnancy and lactation. Mother's milk is a milk blend with the right balance of nutrition needed during pregnancy and lactation.

Specifically, a powdered milk formula can be prepared using the following method.

In other words, the subject matter described herein provides a method for producing a powdered milk formula or mother's milk in which a powdered bacterium related to the genus *Bifidobacterium* is mixed with a prebiotic and/or milk powder to obtain a powdered milk for preventing or treating functional gastrointestinal disorders. For example, described is a method for manufacturing a powdered milk for fortifying mother's milk comprising steps (A) to (C) below:
 (A) culturing the *Bifidobacterium* in a medium containing milk components to obtain a culture;
 (B) spray drying and/or freeze-drying the culture to obtain a cell powder; and
 (C) mixing the powdered bacteria with a prebiotic and/or powdered milk to obtain a powdered milk for preventing or treating functional gastrointestinal disorders.

A food composition can be a simple supplement for preventing or treating functional gastrointestinal disorders. A supplement for the prevention or treatment of functional gastrointestinal disorders can be produced using the following method.

Specifically, a method is provided for producing a supplement for the prevention or treatment of functional gastrointestinal disorders comprising steps (A) and (B) below:
 (A) mixing a prebiotic, *Bifidobacterium* bacterium, and excipient together to obtain a mixture; and
 (B) tableting the mixture.

The amount of *Bifidobacterium breve* MCC1274 (FERM BP-11175) in a food or beverage product according to the present technology can be freely selected as long as the effects of the present technology are not impaired. In the present technology, the amount of *Bifidobacterium breve* MCC1274 (FERM BP-11175) in a food or beverage product is preferably from $1\times10^3$ to $1\times10^{12}$ cfu/g of the final composition of the food or beverage product. In terms of the administered dose, it is at least $1\times10^3$ cfu per day, preferably at least $1\times10^6$ cfu per day, more preferably at least $1\times10^8$ cfu per day, and even more preferably at least $2\times10^{10}$ cfu per day. In the present technology, a food or beverage product preferably comprises from $10^6$ to $10^{12}$ cfu of *Bifidobacterium breve* MCC1274 (FERM BP-11175) per serving. Here, cfu means colony forming unit. In the case of dead bacteria, cfu/g or cfu/ml can be converted to cells/g or cells/ml. In the case of disrupted bacteria, the number of cells (cells/g) prior to disruption can be indicated in terms of weight.

Functionally Labeled Food and Beverage Products

A food or beverage product defined in the present technology can be provided and sold as a food or beverage product labeled by intended use (especially, health use) or function. "Labeled" includes all acts performed in order to inform consumers of the intended use. Any expression used to evoke or infer the intended use, regardless of the purpose of the label, the content of the label, the object to be labeled, or the medium is considered a "labeling" act in the present technology.

A "label" preferably uses expressions enabling the consumer to clearly identify the intended use. This includes descriptions of the intended use on the food or beverage product or packaging for the product which is displayed for shipment and delivery, descriptions of the intended in price lists and business documents related to import and advertising, and descriptions of the intended use in information related to the food or beverage product provided using an electromagnetic method (via the internet, etc.).

The content of the label is preferably approved by the relevant government authorities (for example, a label approved by relevant governmental organizations and used in an approved manner). Preferably, the label content is included in packaging, containers, catalogs, brochures, and point-of-purchase (POP) advertising.

The labeling also indicates whether the product is a health food, functional food, patient food, enteral nutrition food, special purpose food, health-promoting food, specific health food, functional-labeled food, nutritional food, or quasi-drug. These include labels approved by consumer agencies in accordance with, for example, special health product procedures, function-claiming product procedures, and analogous procedures. Specific examples include labels indicating a specific health food, labels indicating a specific health food with conditions, labels indicating a function-claiming product, labels indicating effects on bodily structures and functions, and labels indicating reduced risk of disease. For typical examples see the labels for specific health foods (especially, the intended health effect) included in Ordinance for Enforcement of the Health Promotion Act (Ordinance No. 86 of the Japanese Ministry of Health, Labor and Welfare dated Apr. 30, 2003, and the labels for function-claiming products included in Food Labeling Act (Act No. 70 of 2013).

The wording used in these labels is not necessarily restricted to wording on the prevention or amelioration of functional gastrointestinal disorders. It may also include wording within the scope of the present technology regarding the prevention, treatment and/or amelioration of disorders related to the prevention or amelioration of functional gastrointestinal disorders. For example, the wording may be based on intended uses which are recognized by consumers as having a preventative or ameliorative effect on functional gastrointestinal disorders such as "for those who have recurring diarrhea and constipation", "for those who have an unsettled stomach", and "for those who have stomachaches due to stress".

<Pharmaceutical and Quasi-Drug Products>

A composition for preventing or ameliorating a functional gastrointestinal disorder according to the present technology can be added to an existing pharmaceutical product or quasi-drug ("pharmaceutical product etc." below) or mixed with the ingredients of a pharmaceutical product etc. to prepare a novel pharmaceutical product etc.

When a composition for preventing or ameliorating a functional gastrointestinal disorder according to the present technology is to be used in a pharmaceutical product etc., the pharmaceutical product etc. can be formulated in the desired dosage form depending on whether the method of administration is oral or parenteral. There are no particular restrictions on the dosage form. In the case of oral administration, the composition can be formulated in the form of a solid preparation such as a powder, granules, tablet, lozenge, or capsule; or a liquid preparation such as a solution, syrup, suspension, or emulsion. In the case of parenteral administration, the composition can be formulated as a suppository, spray, inhalant, ointment, patch, or injectable. Formulation as an orally administered dosage form is preferred. It can be formulated in the desired dosage form using any method common in the art.

The composition may be compounded with a suitable carrier during formulation. In addition to a composition for preventing or ameliorating a functional gastrointestinal disorder according to the present technology, components ordinarily used in the formulation process include excipients, pH adjusters, coloring agents, and flavoring agents. Another component having a known or anticipated effect of preventing, ameliorating and/or treating a disease or symptom can be included if appropriate.

Depending on the dosage form, the carrier in the formulation can be an organic or inorganic carrier. Examples of carriers in solid formulations include excipients, binders, disintegrants, lubricants, stabilizers, and flavoring agents.

Examples of excipients include sugar derivatives such as lactose, sucrose, glucose, mannitol, and sorbite; starch derivatives such as corn starch, potato starch, α-starch, dextrin, and carboxymethyl starch; cellulose derivatives such as crystalline cellulose, hydroxypropyl cellulose, hydroxypropyl methylcellulose, carboxymethylcellulose, and carboxymethylcellulose calcium; gum arabic; dextran; pullulan; silicate derivatives such as light anhydrous silicic acid, synthetic aluminum silicate, and magnesium aluminometasilicate; phosphate derivatives such as calcium phosphate; carbonate derivatives such as calcium carbonate; and sulfate derivatives such as calcium sulfate.

In addition to the excipients mentioned above, examples of binders include gelatins, polyvinyl pyrrolidone, and macrogol.

In addition to the excipients mentioned above, examples of disintegrants include chemically modified starches such as croscarmellose sodium, carboxymethyl starch sodium, and crosslinked polyvinylpyrrolidone, as well as cellulose derivatives.

Examples of lubricants include talc; stearic acid; metallic stearates such as calcium stearate and magnesium stearate; colloidal silica; waxes such as Veegum and spermaceti; boric acid; glycol; carboxylic acids such as fumaric acid and adipic acid; carboxylic acid sodium salts such as sodium benzoate; sulfates such as sodium sulfate; leucine; lauryl sulfate such as sodium lauryl sulfate and magnesium lauryl sulfate; silicas such as anhydrous silicic acid and silicic acid hydrate; and starch derivatives.

Examples of stabilizers include para-hydroxybenzoic acid esters such as methylparaben and propylparaben; alcohols such as chlorobutanol, benzyl alcohol, and phenylethyl alcohol; benzalkonium chloride; acetic anhydride; and sorbic acid.

Examples of flavoring agents include sweetening agents, acidulants, and flavorings. Solvents such as water and flavoring agents are examples of carriers used in solutions for oral administration.

The amount of *Bifidobacterium breve* MCC1274 (FERM BP-11175) in a pharmaceutical product etc. according to the present technology can be freely selected as long as the effects of the present technology are not impaired. In the present technology, the amount of *Bifidobacterium breve* MCC1274 (FERM BP-11175) in a pharmaceutical product etc. is preferably from $1\times10^3$ to $1\times10^{12}$ cfu/g of the final composition of the pharmaceutical product etc. In terms of the administered dose, it is at least $1\times10^3$ cfu per day, preferably at least $1\times10^6$ cfu per day, more preferably at least $1\times10^8$ cfu per day, and even more preferably at least $2\times10^{10}$ cfu per day. In the present technology, a pharmaceutical product etc. preferably comprises from $10^6$ to $10^{12}$ cfu of *Bifidobacterium breve* MCC1274 (FERM BP-11175) per packaging unit.

<Feed>

A composition for preventing or ameliorating a functional gastrointestinal disorder according to the present technology can be added to an existing feed or mixed with the ingredients of a feed to prepare a novel feed.

When a composition for preventing or ameliorating a functional gastrointestinal disorder according to the present technology is added to a feed, feed ingredients include cereals such as corn, wheat, barley, and rye; brans such as wheat bran, rice bran, and defatted bran; meals such as corn gluten meal and corn germ meal; animal products such as skimmed milk powder, whey, fish meal, and bone meal; yeasts such as beer yeast; minerals such as calcium phosphate and calcium carbonate; oils and fats; amino acids; and sugars. Examples of feeds include animal feed (pet food, etc.), livestock feed, and fish food.

The amount of *Bifidobacterium breve* MCC1274 (FERM BP-11175) in a feed according to the present technology can be freely selected as long as the effects of the present technology are not impaired. In the present technology, the amount of *Bifidobacterium breve* MCC1274 (FERM BP-11175) in a feed is preferably from $1\times10^3$ to $1\times10^{12}$ cfu/g of the final composition of the feed. In terms of the administered dose, it is at least $1\times10^3$ cfu per day, preferably at least $1\times10^6$ cfu per day, more preferably at least $1\times10^8$ cfu per day, and even more preferably at least $2\times10^{10}$ cfu per day.

The present technology can also adopt the following configurations.

[1] A composition for preventing or ameliorating a functional gastrointestinal disorder whose active ingredient is *Bifidobacterium breve* MCC1274 (FERM BP-11175).

[2] A composition according to [1], wherein the composition prevents or ameliorates constipation or frequent bowel movements, regulates the number of bowel movements, improves stool quality, prevents or ameliorates constipation, prevents or ameliorates bloating, or prevents or ameliorates abdominal discomfort.

[3] A composition according to [1] or [2], wherein the composition relieves stress and/or anxiety symptoms.

[4] A composition according to any one of [1] to [3], wherein the composition prevents or alleviates anger, confusion, tension or fatigue, or improves vitality.

[5] A composition according to any one of [1] to [4], wherein the composition is a pharmaceutical composition.

[6] A composition according to [5], wherein the composition comprises from $10^6$ to $10^{12}$ cfu of *Bifidobacterium breve* MCC1274 (FERM BP-11175) per packaging unit.

[7] A composition according to any one of [1] to [4], wherein the composition is a food or beverage composition.

[8] A composition according to [7], wherein the composition comprises from $10^6$ to $10^{12}$ cfu of *Bifidobacterium breve* MCC1274 (FERM BP-11175) per serving.

[9] A composition according to [7] or [8], wherein the composition is yogurt.

[10] The use of *Bifidobacterium breve* MCC1274 (FERM BP-11175) in an agent for preventing or ameliorating a functional gastrointestinal disorder, a pharmaceutical for preventing or ameliorating a functional gastrointestinal disorder, or a food or beverage product for preventing or ameliorating a functional gastrointestinal disorder.

[11] A method for preventing or ameliorating a functional gastrointestinal disorder, the method comprising administering *Bifidobacterium breve* MCC1274 (FERM BP-11175) to the subject.

[12] A method for preventing or ameliorating a functional gastrointestinal disorder, the method comprising administering *Bifidobacterium breve* MCC1274 (FERM BP-11175) to a subject with normal brain function.

[13] A method for preventing or ameliorating a functional gastrointestinal disorder, the method comprising administering *Bifidobacterium breve* MCC1274 (FERM BP-11175) to a person who is 35 years of age or older.

[14] A method for preventing or ameliorating a functional gastrointestinal disorder, the method comprising administering *Bifidobacterium breve* MCC1274 (FERM BP-11175) to a subject during the autumn and winter seasons.

EXAMPLES

The following is a more detailed description of the present technology with reference to examples. The examples described below are typical examples of the present technology and should not be interpreted as narrowing the scope of the present technology in any way.

Example 1

<Preparation of Test Samples>

Fermented milk products were prepared using the following process with and without *Bifidobacterium breve* MCC1274 (FERM BP-11175). First, raw milk, water as needed, and other components were mixed together, and homogenization and heat sterilization were performed in the usual manner. Freeze-dried powder of *Bifidobacterium breve* MCC1274 (FERM BP-11175) and lactic acid bacterium starter were added (inoculated) in the heat-sterilized milk preparation, and fermentation was allowed to occur at a constant fermentation temperature. When the pH reached the target value, the curds were broken up by stirring and cooled to 10° C. or lower to obtain the fermented milk used as a test sample. Meanwhile, sterilized milk preparation to which only lactic acid bacteria starter had been added (inoculated) was used in the same process to produce the fermented milk used as the control sample. It was determined that the test sample and the control sample were indistinguishable in terms of appearance, color, and taste.

<Test Subjects>

Healthy subjects (with a BMI from 25 to 30) aged 20 to 65 years at the time of consent were registered in the clinical trial as subjects. In addition, 140 persons who did not violate exclusion criteria (1) to (6) below were selected as subjects based on body composition measurements, blood tests, and physician interviews.

(1) Persons with a medical history including serious disease
(2) Persons receiving medical treatment for lifestyle-related disease (diabetes, high blood pressure, dyslipidemia)
(3) Persons with drug allergies or serious food allergies
(4) Persons who are pregnant, intending to become pregnant during the trial period, or are breastfeeding
(5) Persons who are heavy smokers and/or heavy drinkers
(6) Persons deemed to be unsuitable as a test subject by the examining doctor or assisting doctor based on the subject's background, physical findings, or the interview.

Specific background factors on the subjects are shown in Table 1 below. There was no significant difference in age between the control group and the test group.

TABLE 1

|  | Control Group | Test Group | Difference |
|---|---|---|---|
| No. of Subjects (Persons) | 70 | 70 | N.S. |
| Age | 46.8 ± 8.7 | 47.6 ± 8.6 | N.S. |

<Testing Methodology>

A randomized, double-blind, placebo-controlled, parallel-group comparison study was conducted. After a two-week pre-observation period, 70 of the 140 test subjects were assigned to either the group taking the control sample (the "control group" below) or the group taking the test sample ("test group" below). The subjects in both groups ingested either the test sample or the control sample once a day, morning, day or night, for 12 consecutive weeks. The number of viable *Bifidobacterium breve* MCC1274 (FERM BP-11175) bacterial in the test sample was at least 100 million per day (per unit). In other words, the daily intake of the test group was at least 100 million viable *Bifidobacterium breve* MCC1274 (FERM BP-11175) bacteria.

In order to evaluate the intestinal regulating effect of the ingested test sample, the number of bowel movements per day was measured from a point in time before the trial through the 12th week of the trial. Also, the characteristics of the subjects' stools were observed each week based on the index shown in Table 2 (the Bristol stool scale). The number of bowel movements was counted as the total number per week, and the stool quality was the average value for each week.

TABLE 2

| Bristol Stool Scale | | |
|---|---|---|
| 1 | Separate but hard | Separate hard lumps, like rabbit pellets |
| 2 | Hard | Hard, sausage-like |
| 3 | Somewhat hard | Sausage-like with surface cracks |
| 4 | Ordinary | Sausage or snake-like with smooth, soft surface |
| 5 | Somewhat soft | Soft, semi-hard with clear-cut edges |
| 6 | Muddy | Soft, irregular pieces with loose edges, muddy |
| 7 | Watery | Entirely liquid with no solid pieces, watery |

In order to assess temporary moods, a "POMS 2 short version for adults" mood profile examination was given before the study and during the 12th week of the study, and the total score was converted to T scores according to the Japanese manual.

<Statistical Analysis>

A review of blinded results was conducted to exclude persons who did not meet analysis criteria established in advance (namely, those who had an ingestion rate of less than 80% those who violated the medicine dose or ingested prohibited foods, and those who were found to have violated or deviated significantly from the test plan). Because none of them were excluded, an analysis of efficacy was conducted on all 140 subjects. Statistical significance testing was conducted using a paired t-test for comparisons before and after intake, and an unpaired t-test for comparison of values between the control group and the test group. In addition, a stratification analysis was conducted on the bowel movement situation of those who had a low bowel movement frequency (less than 4 times a week) and those who had a high bowel movement frequency (more than 10 times a week) during the pre-observation period (before intake).

<Results>

The results for bowel movement frequency, changes in bowel movement frequency, and stool quality for subjects whose bowel movement frequency before intake was four or fewer times a week are shown in FIG. 1 to FIG. 3. The results for bowel movement frequency, changes in bowel movement frequency, and stool quality for subjects whose bowel movement frequency before intake was ten or more times a week are shown in FIG. 4 to FIG. 6.

As shown in FIG. 1 and FIG. 2, in subjects with constipation whose number of bowel movements before intake was four or less per week (test group: n=5, control group: n=4), there was almost no change in the number of bowel movements compared to before intake in the control group but a significant increase in number of bowel movements compared to before intake in the test group. Also, in the test group, as shown in FIG. 3, stool quality tended to improve in the direction of ordinary stool quality.

As shown in FIG. 4 and FIG. 5, in subjects whose number of bowel movements before intake was ten or more per week (test group: n=24, control group: n=21), there was increased frequency in the number of bowel movements compared to before intake in the control group but the number of bowel movements compared to before intake was maintained in the test group. Also, in the test group, as shown in FIG. 6, stool quality tended to improve in the direction of ordinary stool quality.

The results of the "POMS 2 short version for adults" mood profile examination are shown in Table 2.

TABLE 3

| T Score | AH | CB | DD | FI | TA | VA | F | TMD Score |
|---|---|---|---|---|---|---|---|---|
| Test Group | 0.1 | −0.3 | 0.1 | −0.4 | −0.5 | 1.2 | 0.3 | −0.4 |
| Control Group | 1.7 | 1.9 | 1.1 | 0.6 | 1.8 | −0.1 | 0.0 | 1.5 |
| p Value (t-test) | 0.10 | 0.01 | 0.24 | 0.33 | 0.03 | 0.32 | 0.82 | 0.03 |

Compared to the control group, the numerical values were lower for Anger-Hostility (AH), Confusion-Bewilderment (CB), Depression-Dejection (DD), Fatigue-Inertia (FI), Tension-Anxiety (TA), and Total Mood Disturbance (TMD) in the test group as shown in Table 3. The numerical values for Confusion-Bewilderment (CB), Tension-Anxiety (TA), and Total Mood Disturbance (TMD) were significantly lower. Compared to the control group, the numerical values for Vigor-Activity (VA) and Friendliness (F) were higher in the test group. It is clear from these results that *Bifidobacterium breve* MCC1274 (FERM BP-11175) effectively improves the mood profile in all of the categories, that is, Anger-Hostility (AH), Confusion-Bewilderment (CB), Depression-Dejection (DD), Fatigue-Inertia (FI), Tension-Anxiety (TA), Total Mood Disturbance (TMD), Vigor-Activity (VA), and Friendliness (F).

The results of the "POMS 2 short version for adults" mood profile examination on subjects whose bowel movement frequency before intake was four or fewer times a week are shown in Table 4.

TABLE 4

| T Score | AH | CB | DD | FI | TA | VA | F | TMD Score |
|---|---|---|---|---|---|---|---|---|
| Test Group | −5.0 | −3.6 | −2.0 | −7.8 | −5.2 | 4.8 | 3.2 | −5.8 |
| Control Group | −0.3 | 0.3 | −2.5 | −0.8 | −1.8 | −1.3 | −1.3 | −1.3 |
| p Value (t-test) | 0.45 | 0.22 | 0.91 | 0.15 | 0.45 | 0.34 | 0.59 | 0.29 |

Compared to the control group, the numerical values were lower for Anger-Hostility (AH), Confusion-Bewilderment (CB), Fatigue-Inertia (FI), Tension-Anxiety (TA), and Total Mood Disturbance (TMD) in the test group as shown in Table 4. Compared to the control group, the numerical values for Vigor-Activity (VA) and Friendliness (F) were higher in the test group. It is clear from these results that constipation was eliminated and the mood profile improved in subjects whose bowel movement frequency before intake was four or fewer times a week.

The results of the "POMS 2 short version for adults" mood profile examination on subjects whose bowel movement frequency before intake was ten or more times a week are shown in Table 5.

TABLE 5

| T Score | AH | CB | DD | FI | TA | VA | F | TMD Score |
|---|---|---|---|---|---|---|---|---|
| Test Group | 0.2 | −0.1 | −0.4 | −0.2 | −0.6 | 1.7 | −0.3 | −0.5 |
| Control Group | 3.6 | 1.2 | 2.2 | 2.4 | 1.7 | 0.6 | −1.9 | 2.2 |
| p Value (t-test) | 0.05 | 0.40 | 0.03 | 0.16 | 0.27 | 0.68 | 0.51 | 0.08 |

Compared to the control group, the numerical values were lower for Anger-Hostility (AH), Confusion-Bewilderment (CB), Depression-Dejection (DD), Fatigue-Inertia (FI), Tension-Anxiety (TA), and Total Mood Disturbance (TMD) in the test group as shown in Table 5. The numerical values for Anger-Hostility (AH) and Depression-Dejection (DD) were significantly lower. Compared to the control group, the numerical values for Vigor-Activity (VA) and Friendliness (F) were higher in the test group. It is clear from these results that stool quality and the mood profile improved in subjects whose bowel movement frequency before intake was ten or more times a week.

Example 2

<Testing Methodology>

A fermented milk product containing *Bifidobacterium breve* MCC1274 (FERM BP-11175) identical to the one in Example 1 was used as the test sample, and a questionnaire was filled out by 11 healthy men and women (BMI: 17.1 to 30.1 kg/m$^2$, average BMI: 22.8±3.6 kg/m$^2$) who were 20 years of age or older on their overall feeling of physical well-being and on the condition of their stomach (pain, bloating, and discomfort) before and after ingestion of the fermented milk product. The subjects ingested the test sample once daily after a meal, in the morning, during day, or at night, for four consecutive weeks. The number of viable *Bifidobacterium breve* MCC1274 (FERM BP-11175) bacteria in the test sample was at least 100 million per day (per unit). In other words, the daily intake of the test group was at least 100 million viable *Bifidobacterium breve* MCC1274 (FERM BP-11175) bacteria.

After ingesting the test sample for four weeks, the answers for overall physical well-being were "good" 9%, "fairly good" 64%, "unchanged" 27%, and "fairly poor" and "poor" 0%. The answers for the condition of their stomach (pain, bloating, and discomfort) were "good" 9%, "fairly good" 46%, "unchanged" 45%, and "fairly poor" and "poor" 0%. The answers for premenstrual upset (stomachache, diarrhea) were better. Specifically, after intake of the test sample, 73% of the test subjects reported that their overall physical well-being was "good" or "fairly good" and none of the test subjects were worse off than before intake. Specifically, after intake of the test sample, 55% of the test subjects reported that the condition of their stomach (pain, bloating, and discomfort) was "good" or "fairly good" and none of the test subjects were worse off than before intake.

Example 3

<Preparation of Test Sample>

The culture solution of Bifidobacterium breve MCC1274 (FERM BP-11175) was concentrated and dried to obtain viable bacterium dry matter. The viable bacterium dry matter was mixed with starch, and capsules were each filled with 345 mg of the mixture to obtain a test sample. Placebo capsules containing 345 mg of starch were prepared as a control sample. Test subjects could not notice differences in appearance, color, and flavor between the test sample and the control sample.

<Test Subjects>

Healthy subjects (with a BMI from 25 to 30) aged 20 or over were registered as test subjects. In addition, persons who did not violate exclusion criteria (1) to (7) below were selected based on body composition measurements, blood tests, and physician interviews.
(1) Persons with a medical history including treatment for serious disease
(2) Persons who suffer from and take medicine for a gastrointestinal disease
(3) Persons receiving medical treatment for lifestyle-related disease (diabetes, high blood pressure, dyslipidemia)
(4) Persons with drug allergies or serious food allergies
(5) Persons who are pregnant, intending to become pregnant during the trial period, or are breastfeeding
(6) Persons who are heavy smokers, heavy drinkers and/or have erratic life habits
(7) Persons deemed to be unsuitable as a test subject by the examining doctor or assisting doctor based on the subject's background, physical findings, or the interview.

Persons who suffer from gastrointestinal disease (2) include persons suffering from and taking medicine for organic diseases such as ulcerative colitis and colorectal cancer, and does not include persons suffering from functional diseases.

Specific background factors on the subjects are shown in Table 6 below. There was no significant difference in age between the control group and the test group.

TABLE 6

|  | Control Group | Test Group | Difference |
|---|---|---|---|
| Subjects (Persons) | 40 | 40 | N.S. |
| Age (in years) | 45.6 ± 8.5 | 45.4 ± 9.8 | N.S. |

<Testing Methodology>

A randomized, double-blind, placebo-controlled, parallel-group comparison study was conducted. After a two-week pre-observation period, the test subjects were assigned to either the group taking the control sample (the "control group" below) or the group taking the test sample ("test group" below). The subjects in both groups took either the test sample or the control sample with water once a day within 30 minutes of a meal, morning, day or night, for 12 consecutive weeks. The daily intake of the test group was 200 million viable Bifidobacterium breve MCC1274 (FERM BP-11175) bacteria.

In order to assess temporary moods, a "POMS 2 short version for adults" mood profile examination was given before the study and during the 12th week of the study, and the total score was converted to T scores according to the Japanese manual. In the test group, the Pittsburgh Sleep Quality Index (PSQI) was given before the study and during the 12th week of the study, and an overall score was calculated based on seven components, namely, sleep quality, sleep latency, sleep duration, habitual sleep efficiency, sleep disturbances, use of sleeping medication, and daytime dysfunction.

<Statistical Analysis>

A review of blinded results was conducted to exclude persons who did not meet analysis criteria established in advance (namely, those who had an ingestion rate of less than 80% those who violated the medicine dose or ingested prohibited foods, and those who were found to have violated or deviated significantly from the test plan). Because none of them were excluded, an analysis of efficacy was conducted on all 80 subjects.

<Results>

The results of the "POMS 2 short version for adults" mood profile examination are shown in Table 7, and the results of the Pittsburgh Sleep Quality Index (PSQI) on the test group are shown in Table 8.

TABLE 7

|  | Control Group | | | Test Group | | |
|---|---|---|---|---|---|---|
|  | Pre-Intake | 12 Weeks | p Value* | Pre-Intake | 12 Weeks | p Value* |
| Anger-Hostility (AH) | 44.6 ± 6.1 | 46.9 ± 6.8 | 0.031 | 45.2 ± 6.6 | 46.3 ± 7.7 | 0.311 |
| Confusion-Bewilderment (CB) | 44.0 ± 6.7 | 47.1 ± 7.4 | 0.004 | 46.6 ± 8.7 | 46.6 ± 8.7 | 1.000 |
| Depression-Dejection (DD) | 45.2 ± 5.7 | 46.8 ± 7.5 | 0.063 | 46.1 ± 7.5 | 47.0 ± 8.3 | 0.275 |
| Fatigue-Inertia (FI) | 43.6 ± 6.2 | 45.1 ± 6.9 | 0.189 | 44.7 ± 8.5 | 46.0 ± 8.6 | 0.077 |
| Tension-Anxiety (TA) | 43.7 ± 5.4 | 45.4 ± 5.9 | 0.055 | 46.7 ± 9.7 | 46.8 ± 8.7 | 0.948 |

TABLE 7-continued

|  | Control Group | | | Test Group | | |
| --- | --- | --- | --- | --- | --- | --- |
|  | Pre-Intake | 12 Weeks | p Value* | Pre-Intake | 12 Weeks | p Value* |
| Vigor-Activity (VA) | 49.4 ± 8.9 | 50.4 ± 8.0 | 0.358 | 52.6 ± 10.1 | 53.1 ± 11.0 | 0.673 |
| Friendliness (F) | 49.3 ± 8.6 | 51.9 ± 9.1 | 0.086 | 52.0 ± 10.4 | 52.4 ± 11.4 | 0.767 |
| Total Mood Disturbance (TMD) | 44.3 ± 5.9 | 46.2 ± 6.7 | 0.032 | 45.3 ± 8.4 | 46.0 ± 9.0 | 0.408 |

The results are shown as mean value plus standard deviation.
*Comparison between groups used average before intake from an unpaired t-test.

TABLE 8

| Before Intake | After Intake | Change |
| --- | --- | --- |
| 3.1 | 2.9 | -0.2 |

The numerical values rose significantly for Anger-Hostility (AH), Confusion-Bewilderment (CB), Depression-Dejection (DD), Tension-Anxiety (TA), and Total Mood Disturbance (TMD) remained low in the control group after 12 weeks whereas these numerical values remained low in the test group as shown in Table 7. It is clear from these results that *Bifidobacterium breve* MCC1274 (FERM BP-11175) effectively improves the mood profile in the categories of Anger-Hostility (AH), Confusion-Bewilderment (CB), Depression-Dejection (DD), Tension-Anxiety (TA), and Total Mood Disturbance (TMD).

As shown in Table 8, the total PSQI score was -0.20 lower after 12 weeks of ingesting the test substance compared to before, and an improvement was seen in all of the categories, namely, sleep quality, sleep latency, sleep duration, habitual sleep efficiency, sleep disturbances, use of sleeping medication, and daytime dysfunction.

PRODUCTION EXAMPLES

The following are production examples of pharmaceutical and food or beverage compositions for preventing or ameliorating functional gastrointestinal disorders.

Production Example 1

*Bifidobacterium breve* MCC1274 (FERM BP-11175) is added to 3 mL of MRS liquid medium, and the solution is anaerobically cultured at 37° C. for 16 hours, concentrated, and freeze-dried to obtain a freeze-dried powder of the bacteria (bacterial powder). The bacterial powder is then uniformly mixed with whey protein concentrate (WPC) and prebiotics (lacturose, raffinose, and galactooligosaccharides) to obtain a composition. Next, 20 g of the composition is dissolved in 200 g of water to obtain a composition for preventing or ameliorating a functional gastrointestinal disorder. Administration of this composition can prevent or ameliorate functional gastrointestinal disorders.

Production Example 2

*Bifidobacterium breve* MCC1274 (FERM BP-11175) is added to 3 mL of MRS liquid medium, and the solution is anaerobically cultured at 37° C. for 16 hours, concentrated, and freeze-dried to obtain a freeze-dried powder of the bacteria (bacterial powder). The bacterial powder is then uniformly mixed with a dry powder of milk protein concentrate (MPC 480 from Fontera, protein content 80 wt %, casein protein:whey protein=approx. 8:2) and prebiotics (lacturose, raffinose, and galactooligosaccharides) to obtain a composition. Next, 20 g of the composition is dissolved in 200 g of water to obtain a composition for preventing or ameliorating a functional gastrointestinal disorder. Administration of this composition can prevent or ameliorate functional gastrointestinal disorders.

Production Example 3

*Bifidobacterium breve* MCC1274 (FERM BP-11175) is added to 3 mL of MRS liquid medium, and the solution is anaerobically cultured at 37° C. for 16 hours, concentrated, and freeze-dried to obtain a freeze-dried powder of the bacteria (bacterial powder). Next, prebiotics (lacturose, raffinose and galactooligosaccharides) and crystalline cellulose are placed in a stirring granulator and mixed together. Afterwards, purified water is added to granulate, and the granulate is dried to obtain a granulate (pharmaceutical composition) containing bacterial extract, prebiotics, and an excipient. Administration of this composition can prevent or ameliorate functional gastrointestinal disorders.

Production Example 4

The following is a method used to produce a fermented milk product containing *Bifidobacterium breve* MCC1274 (FERM BP-11175). First, raw milk, water as needed, and other components are mixed together, and homogenization and heat sterilization are preferably performed. Homogenization and heat sterilization can be performed in the usual manner. A lactic acid bacteria starter is added (inoculated) to the heat-sterilized milk preparation, and fermentation is carried out by maintaining the temperature at a predetermined fermentation temperature to obtain a fermented product. The fermentation forms curds. The lactic acid bacteria starter can use any lactic acid bacteria commonly used in yogurt such as *Lactobacillus bulgaricus, Lactococcus lactis*, or *Streptococcus thermophilus*. When the pH reaches the target value, the curds are broken up by stirring and cooled to 10° C. or lower to obtain a fermented product. By cooling to 10° C. or lower, the activity of the lactic acid bacteria can be reduced to suppress the formation of acid. Next, the fermented product obtained in the fermentation step is subjected to heat treatment to obtain a heated fermented product (heat-treated fermented product). By heating the fermented product sufficiently, production of acid by lactic acid bacteria can be prevented in the heated fermented product. In this way, any decrease in pH can be suppressed during the subsequent production steps and/or during storage of the concentrated fermented milk product containing *Bifidobacterium*. This improves the survival rate of the *Bifidobacterium*. Next, *Bifidobacterium breve* MCC1274 (FERM BP-11175) and prebiotics (lacturose, raffinose and galactooligosaccharides) are added to the fermented product obtained in the heat treatment step. The amount of *Bifidobacterium breve* MCC1274 (FERM BP-11175) added to the heated fermentation product is preferably from $1\times10^7$ to $1\times10^{11}$ cfu/ml and more preferably from $1\times10^8$ to $1\times10^{10}$ cfu/ml. In the case of dead *Bifidobacterium breve* MCC1274 (FERM BP-11175), cfu/ml can be converted to cells/ml. After heating, *Bifidobacterium breve* MCC1274 (FERM BP-11175) and prebiotics are added to the fermented product, which is then concentrated. The concentration step can be performed using any concentration method common in the art. For example, centrifugation or membrane separation can be used. In the centrifugation method, whey is removed from the concentrate (heated fermented product containing added bifidobacteria and prebiotics) to increase the amount of concentrated fermented milk containing bifidobacteria and prebiotics in terms of solid content. Administration of this fermented milk product can prevent or ameliorate functional gastrointestinal disorders.

Production Example 5

The following is a method used to produce an infant formula containing *Bifidobacterium breve* MCC1274 (FERM BP-11175). Here, 10 kg of desalted milk whey protein powder (from Mirai), 6 kg of milk casein powder (from Fonterra), 48 kg of lactose (from Mirai), 920 g of a mineral mixture (from Tomita Pharmaceuticals), 32 g of a vitamin mixture (from Tanabe Seiyaku), 500 of lactulose (from Morinaga Milk Industries), 500 g of raffinose (from Nippon Kanso Sugar), and 900 g of galacto-oligosaccharide liquid sugar (from Yakult Pharmaceutical Industries) are heat-dissolved in 300 kg of hot water at 90° C. for 10 minutes, 28 kg of a prepared fat (from Taiyo Yushi Corporation) is added, and the solution is homogenized. Afterwards, sterilization, concentration, and spray-drying are performed to prepare about 95 kg of infant formula powder. Next, 100 g of *Bifidobacterium breve* MCC1274 (FERM BP-11175) powder ($1.8\times10^{11}$ cfu/g from Morinaga Milk) dispersed in starch is added to prepare about 95 kg of infant formula powder containing *Bifidobacterium* and oligosaccharides. When the resulting powder is dissolved in water to obtain liquid infant formula with a standard solid concentration of 14% (w/V), the *Bifidobacterium* count in the liquid infant formula is $2.7\times10^9$ cfu/100 mL. Administration of this infant formula can prevent or ameliorate functional gastrointestinal disorders.

The invention claimed is:

1. A method for treating specific symptoms of a functional gastrointestinal disorder in a subject in need thereof, the method comprising administering a composition consisting essentially of *Bifidobacterium breve* MCC1274 (FERM BP-11175) to the subject;
   wherein the specific symptoms are selected from the group consisting of:
      i) constipation,
      ii) frequent bowel movements,
      iii) bloating,
      iv) abdominal discomfort, and
      v) combinations thereof;
   wherein as a result of said treating, the number of bowel movements is regulated in said subject and/or stool quality is improved in said subject.

2. The method for treating a functional gastrointestinal disorder of claim 1, wherein the subject has normal brain function.

3. The method for treating a functional gastrointestinal disorder of claim 1, wherein the subject is a person who is 35 years of age or older.

4. The method for treating a functional gastrointestinal disorder of claim 1, wherein said administering occurs during the autumn and winter seasons.

5. The method for treating a functional gastrointestinal disorder of claim 1, wherein said disorder is accompanied by an anxiety disorder.

6. The method for treating a functional gastrointestinal disorder of claim 1, wherein said disorder is accompanied by stress.

7. A method for specific symptoms of a functional gastrointestinal disorder in a subject in need thereof, the method comprising administering a composition consisting essentially of *Bifidobacterium breve* MCC1274 (FERM BP-11175) to the subject;
   wherein said functional gastrointestinal disorder is selected from the group consisting of:
      i) non-erosive reflux disease (NERD),
      ii) functional dyspepsia (FD),
      iii) irritable bowel syndrome (IBS),
      iv) functional constipation,
      v) functional diarrhea,
      vi) functional abdominal pain,
      vii) functional abdominal distension,
      viii) epigastric pain syndrome (EPS),
      ix) postprandial distress syndrome (PDS), and
      x) combinations thereof.

* * * * *